US010825560B1

(12) United States Patent
Berenson (10) Patent No.: US 10,825,560 B1
(45) Date of Patent: Nov. 3, 2020

(54) INFUSION MONITORING DEVICE AND PATIENT COMPLIANCE SYSTEM

(71) Applicant: Berenson Consulting Group Inc., Dallas, TX (US)

(72) Inventor: Mitchell Thomas Berenson, Royse City, TX (US)

(73) Assignee: Berenson Consulting Group Inc., Dallas, TX (US)

( * ) Notice: Subject to any disclaimer, the term of this patent is extended or adjusted under 35 U.S.C. 154(b) by 0 days.

(21) Appl. No.: 16/733,492

(22) Filed: Jan. 3, 2020

(51) Int. Cl.
| *A61M 5/50* | (2006.01) |
| *G16H 20/17* | (2018.01) |
| *G16H 40/67* | (2018.01) |
| *A61M 5/172* | (2006.01) |

(52) U.S. Cl.
CPC ............ *G16H 20/17* (2018.01); *A61M 5/172* (2013.01); *G16H 40/67* (2018.01); *A61M 2205/3368* (2013.01); *A61M 2205/3584* (2013.01); *A61M 2205/502* (2013.01); *A61M 2205/52* (2013.01)

(58) Field of Classification Search
CPC ....... G16H 20/17; A61M 5/168; A61M 5/172; A61M 5/1413; A61M 5/14244
See application file for complete search history.

(56) References Cited

U.S. PATENT DOCUMENTS

| 5,625,152 | A | 4/1997 | Pandorf et al. |
| 6,212,946 | B1 | 4/2001 | Naegele et al. |
| 6,503,221 | B1 | 1/2003 | Briggs et al. |
| 6,824,528 | B1 | 11/2004 | Faries, Jr. et al. |
| 7,896,834 | B2 | 3/2011 | Smisson, III et al. |
| 9,726,167 | B2 | 8/2017 | Schweitzer et al. |
| 10,434,253 | B2 | 10/2019 | DiPerna et al. |
| 2003/0158547 | A1 | 8/2003 | Phan |
| 2004/0028118 | A1 | 2/2004 | Sidoni |
| 2011/0110281 | A1 | 5/2011 | Mehta et al. |
| 2014/0171868 | A1* | 6/2014 | Zhang ............... A61M 5/14228 604/111 |
| 2018/0318524 | A1* | 11/2018 | Roth ....................... A61M 5/44 |
| 2019/0358387 | A1* | 11/2019 | Elbadry .................. A61M 1/28 |

FOREIGN PATENT DOCUMENTS

| AU | 2018200015 B2 | 1/2018 |
| CN | 202909221 U | 5/2013 |
| CN | 105833397 A | 8/2016 |
| JP | 2012228481 A | 11/2012 |

OTHER PUBLICATIONS

Beth Miller, HIVE Team Seeks to Help with Patient Compliance with Home Treatment, website, Jun. 5, 2019, McKelvey School of Engineering at Washington University in St. Louis, https://engineering,wustl.edu/news/Pages/HIVE-team-seeks-to-help-with-patient-compliance-with-home-treatment.aspx.
Joe Beggs, Sai Dodda, Allie Frank, Glen Kleinshmidt, Chris Sleckman, Improving Non-Compliance in IV Medication and Outpatient Parenteral Antimicrobial Therapy Patients, presentation, Apr. 13, 2019, Sling Health, Washington University in St. Louis, United States of America.

* cited by examiner

Primary Examiner — Hongmin Fan
(74) Attorney, Agent, or Firm — Hitchcock Evert LLP (57) ABSTRACT

An infusion monitoring device (IMD) for facilitating infusion pump medication treatment compliance. The IMD having at least one sensor to monitor data on a tube extending from an infusion pump. The IMD may be part of a compliance system. The IMD able to collect data and communicate data to a network for remote compliance analysis. The system provides compliance feedback to support the patient and improve compliance with the treatment process.

18 Claims, 5 Drawing Sheets

INFUSION MONITORING DEVICE AND PATIENT COMPLIANCE SYSTEM

FIELD OF THE DISCLOSURE

The invention relates generally to sensors for compliance systems.

BACKGROUND

Infusion systems allow patients to continue their medical treatment at home or at a remote location after they have left a medical facility, such as hospital. Such systems facilitate a slow and steady flow of medicine into the patient. The treatment plan may require ongoing periodic treatments for a period of time in order to fully treat a condition. However, patients do not always follow the treatment plans as proscribed, and some outright refuse to treat themselves. When compliance visits are expected, some patients even dump medications to fake compliance. These non-compliant patients are more likely to have negative health outcomes, including amputations, readmissions and even death.

Infusion treatments may use electronic infusion pumps (i.e., pumps that operate based on electric motors or drivers) or mechanical infusion pumps (i.e., pumps that use non-electric mechanical force). While most hospitals and medical facilities use electronic infusion pumps, many remote or home treatments use mechanical infusion pumps, such as elastomeric ball pumps. The elastomeric pumps are driven by the elastic properties in the container and include flow regulators, such as a steel cannula, to control the flow rate to the patient.

Electronic infusion pumps, including portable versions, may include heating features to raise the temperature of medicines or infusion fluids that are kept in cold storage. Managing the temperature of fluids to the patient is important for patient comfort and to avoid negative physiological effects that can occur due to the introduction of cold fluids.

For mechanical infusion pumps, the pump, which includes the infusion fluid, is typically set out for a given amount of time to allow the fluid temperature to rise toward room temperature. After the set time elapses, the mechanical infusion pump is connected to the patient line and treatment begins.

Because some patients fail to follow treatment plans, compliance protocols may be implemented for patient-managed treatments at remote or home locations. Compliance benefits the patient as well as the hospital and payors, insurance companies, Medicare, etc., by reducing the likelihood of a relapse or even death.

Some portable electronic infusion pumps include electronic data logging features to record treatments. These data logs are recorded in an electronic memory device and may be periodically collected when the patient is in a medical facility or a mobile clinician visits the patient. Some electronic pumps may include computer connections or communication components to send the data log to a database. These devices may also include heating components, pressure sensors and regulation systems to prevent improper delivery.

Unlike electronic pumps, mechanical infusion pumps do not have data logging capabilities or integrated systems for confirming treatments are conducted properly. These pumps are typically single-use pumps that are disposed of by a person after use. As such, compliance often requires a person to visit the remote or home location to observe a treatment or check the stored medication to determine if the correct amount is remaining. This leaves multiple avenues for noncompliance that may not be adequately confirmed, such as whether the patient is properly administering treatment at the right time and in the correct manner or if the patient is disposing of medicine.

SUMMARY

The present disclosure teaches an infusion monitoring device (IMD) and patient compliance system for infusion pumps. The compliance system works for all infusion pumps, including mechanical infusion pumps, such as elastomeric ball pumps. Because the IMD is agnostic to the infusion pump, it provides a compliance testing aid applicable to remote and home infusion environments that did not previously have compliance testing aid options available. The IMD may further reduce the psychological effect associated with loneliness, which can lead to noncompliance—e.g., a patient's belief that because they are alone, no one cares about whether they take their medication. In some embodiments, the IMD connects with the patient's social and clinical support structure.

In some embodiments, an IMD includes a housing having a foldable cap that is biased in a closed position, which abuts a side of the housing. Embodiments may include a spring, elastic or other biasing feature to connect the foldable cap to the housing. The foldable cap and the abutting side of the housing may define a tunnel or path into which a tube fits. Embodiments may include corresponding channels on the foldable cap and the side of the housing that combine to form the tube tunnel. When used in the compliance system, the tunnel may fit around an infusion pump tube and hold the sensor to the tube.

In some embodiments, the housing includes a flow rate sensor (e.g., temperature sensors, bubble sensors, pressure sensors, etc.), control electronics (e.g., a microprocessor, a central processing unit, a microcontroller, etc.), communication components (e.g., a cellular chip, Wi-Fi chip, etc.), memory and a power source. A location component (e.g., a global positioning system (GPS) module, LORAN module, etc.) may be included in some embodiments. In some embodiments, the IMD may include a control interface, such as a switch or button, for a user to control the device. Some embodiments may include a light, a display, a speaker or other output to provide operational feedback to the user.

In some embodiments, a temperature sensor may be located in or abut the tunnel to measure the temperature of the tube. The temperature sensor may take periodic temperature measurements or provide constant temperature information. The temperature information may be stored in the memory. In some embodiments, the temperature information may be sent, whether directly or indirectly through stored memory, through the communication component to other system components In some embodiments, the IMD is attached to the tube extending from a mechanical infusion pump. To attach the IMD to the tube, the foldable cap is opened and the tube is placed in the channel in the side of the housing and then the foldable cap is closed against the tube. The IMD may take measurements, such as the temperature, of the tube. In some embodiments, the temperature sensor or the control electronics may be configured to determine the temperature of a fluid within the tube.

In some embodiments, the IMD may include a connector or latch to hold the foldable cap against the housing. The connector may include a snap-fit, button, friction connectors or other connector components. In some embodiments, the IMD includes a release, which disengages a connector. In some embodiments, a separate sensor may determine if the connector is engaged or disengaged.

Embodiments of the IMD may include additional sensors for beginning operation. In some embodiments, an engagement sensor may cause the monitoring process to begin when the IMD is connected to a tube. An inertial measurement unit may be incorporated to begin the process when the IMD is moved. In rechargeable embodiments, the IMD may include a charging sensor and begin the process when the charging connection is disengaged.

In some embodiments, the IMD is a compliance system feature. The compliance system may include the IMD, a communication network, a cloud system and a monitoring system having a compliance database to receive and store compliance information from the IMD.

In some embodiments, the compliance database may also receive patient treatment plans corresponding to IMDs. The system may use de-identified data to link the treatment plan with the compliance information from the IMD. In some embodiments, the monitoring system includes a computer, including an analysis system, to determine if the received compliance information follows the expected treatment from the treatment plan.

In some embodiments, the system may also include a user device for the patient or another designated person, such as the patient's doctor, agent, representative or decision-maker. In the event that a compliance discrepancy is identified, the computer or compliance database may send a communication to the patient or their designated person. In some embodiments, the system may be designed to send reminder correspondence prior to any compliance concerns.

In some embodiments, the IMD's communication module may be configured to receive signals from the system. The IMD may further provide an output to the patient based on the system signals, such as a reminder light, an audible beep or a vibratory alert. In some embodiments, the IMD may include a display to show stored messages corresponding to compliance notices and reminders. In other embodiments, the compliance notices and reminders may be sent to a user's mobile phone for display.

In some embodiments of the compliance system, the patient will remove the mechanical infusion pump containing infusion fluids, such as medicine, insulin, antibiotics, etc., from cold storage and attach the IMD to the infusion pump tube. When the IMD is attached, it may begin sensing the temperature of the tube automatically or based on a user selection. The patient will then allow the pump and IMD to rest for a proscribed period of time while the fluid temperature increases toward room temperature. While resting, the IMD will continue to sense the temperature and store or transmit the readings.

A BRIEF DESCRIPTION OF THE DRAWINGS

Embodiments will now be described, by way of example only, with references to the accompanying drawings in which.

DETAILED DESCRIPTION

While this invention may be embodied in many different forms, there will herein be described in detail preferred embodiments of the invention with the understanding that the present disclosure is to be considered as an exemplification of the principles of the invention and is not intended to limit the broad aspects of the invention to the embodiments illustrated. It will be understood that the invention may be embodied in other specific forms without departing from the spirit or central characteristics thereof. The present embodiments, therefore, are to be considered in all respects as illustrative and not restrictive, and the invention is not to be limited to the details given herein.

The device is referred to as an "infusion monitoring device" for context in the examples provided. One having ordinary skill in the art will understand that the device taught is a tube monitoring device that may be used in additional environments and contexts.

Figure 1A:
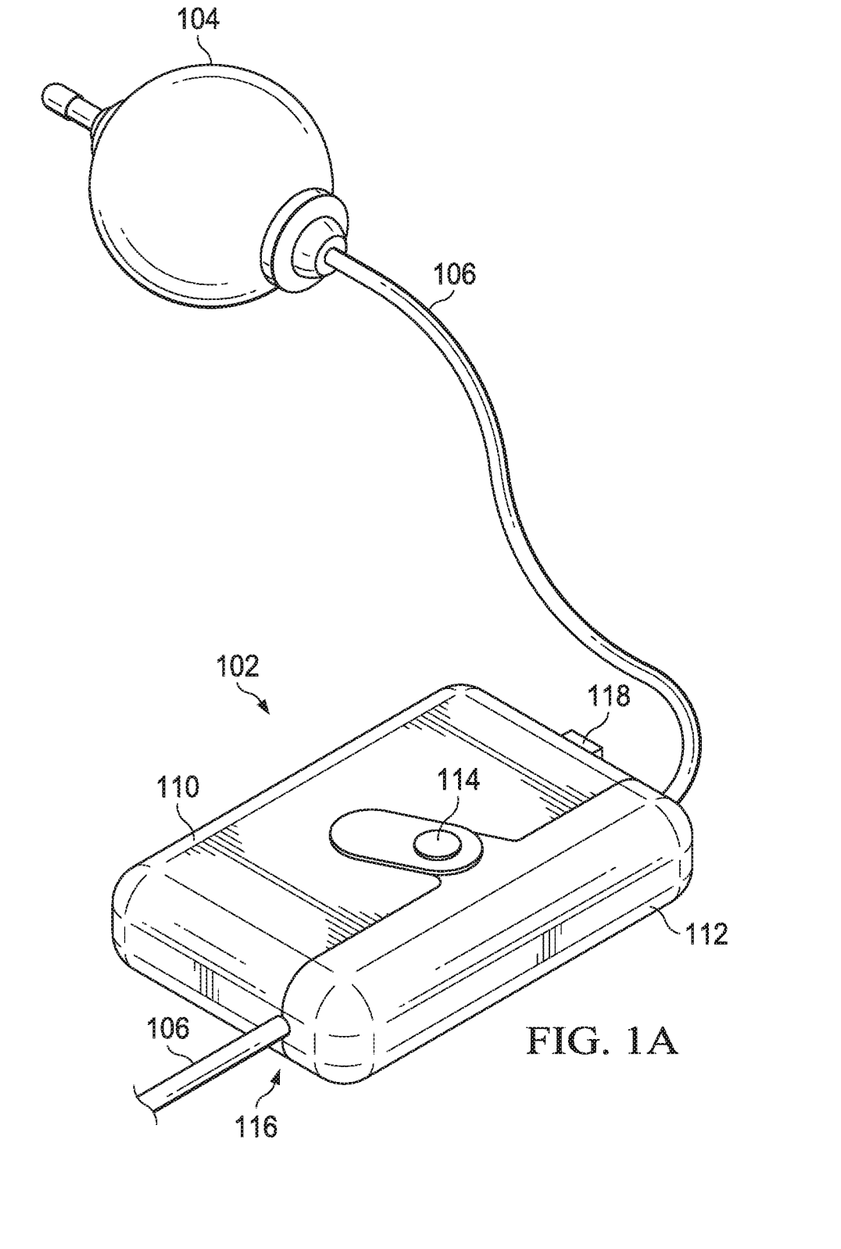
FIGS. 1A and 1B are embodiments of an infusion pump and infusion monitoring device.

FIG. 1A depicts an infusion monitoring device (IMD) 102 attached to a tube 106 extending from infusion pump 104. The infusion pump 104 in this embodiment is depicted as an elastomeric ball infusion pump, which uses pressure created by elastic force to move medicine or other infusion fluid through tube 106. The elastomeric ball infusion pump is an example of a mechanical infusion pump. Those having ordinary skill in the art will recognize that the IMD 102 may be used with other infusion pumps. In addition, the IMD 102 may be attached to tubes 106 extending from other infusion pumps, fluid transfer systems or other components.

The IMD 102 includes a main body or housing 110 and a slidable cap 112. The side of housing 110 and the slidable cap 112 include corresponding channels that form a tunnel 116 when the slidable cap 112 is closed against the housing 110. In other embodiments, alternate movable cap configurations to the slidable cap 112 may be used to allow an open position and a closed position, such as a hinged cap. The tunnel 116 fits around the tube 106, and attaches the IMD 102 to the tube 106. Cap control 114 allows a user to move the slidable cap 112 to an open position for a tube 106 to be fit into place.

Figure 1B:
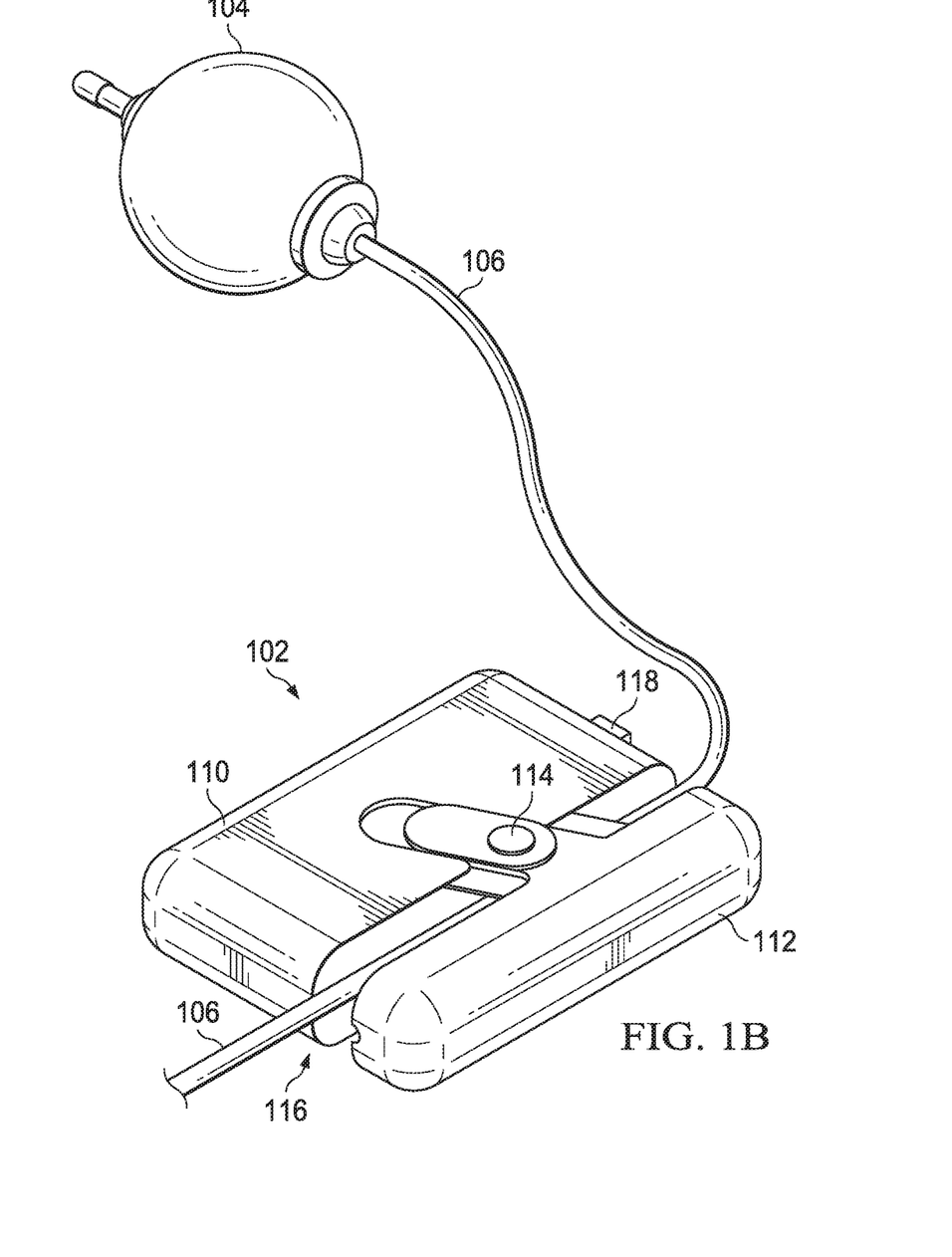

FIG. 1B shows the IMD 102 with cap control 114 moved to a second position, causing slidable cap 112 to be in an open configuration. In this open configuration, the IMD 102 may be connected to or removed from the tube 106.

In this embodiment, the IMD 102 includes a switch 118 on the main housing 110. The switch 118 may be used as a control to turn the IMD 102 on and off. Other embodiments may be configured to automatically turn on and off based on the movement or operation of the IMD 102. For example, the IMD 102 may turn on and begin a monitoring process when the slidable cap 112 is opened then closed by the cap control 114. In such embodiment, the IMD 102 may include a sensor or other component within or adjacent the tunnel 116 to determine if a tube 106 is in the tunnel 116. It a tube 106 is present, the IMD 102 will turn on. Conversely, when a tube 106 is not present, the IMD 102 may turn off or remain off.

Figure 2:
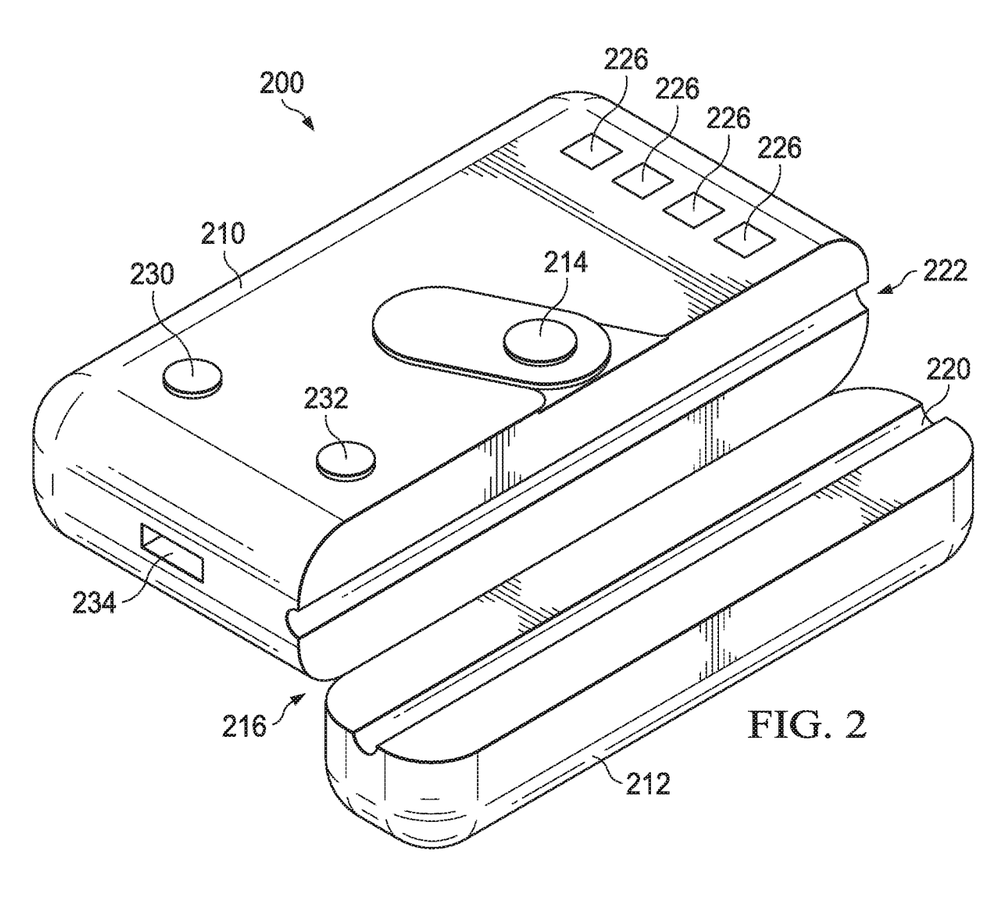
FIG. 2 is an embodiment of the infusion monitoring device.

FIG. 2 illustrates an alternative embodiment of an infusion monitoring device 200. Similar to IMD 102, this embodiment includes a main body 210 and a hinged cap 212. The IMD 200 is shown in an open configuration with the hinged cap 212 attached to the main body 210 at joint 216. The joint 216 may be a hinged connection attaching two pieces together. Alternatively, the main body 210 and the hinged cap 212 may be created together with the joint 216 configured to allow the hinged cap 212 to flex between an open and closed position. For example, the joint 216 may have a plastic or polymer section that is thinner than the housing. The thinner section may allow for bending or flexing.

In some embodiments, the joint 216 may include a spring or other resilient component to bias the hinged cap 212 to the closed position abutting the side of the main body 210. The IMD 200 may include a latch, clip or other feature to hold the hinged cap 212 in place once it is in a closed position.

The IMD 200 also includes a button 214 to control the IMD 200. In some embodiments, the button 214 may control a latch mechanism to release the hinged cap 212 from the main body 210 in order to remove the IMD 200 from a tube 106 or connect it to a tube 106. Alternatively, the button 214 may be used to select an operation or provide system feedback.

The housing channel 222 is located on the side of the housing 210, and cap channel 220 is located in the hinged cap 212. When the housing 210 and hinged cap 212 are in a closed configuration, the housing channel 222 and cap channel 220 align to create a tunnel. A tube is held in this tunnel during operation of the IMD 200.

The IMD 200 includes sensors to measure tube information. For example, the IMD 200 may include temperature sensors to determine the tube temperature. Additional sensors may be within the housing 210 that have sensing surfaces in or against the housing channel 222. For example, a flow rate sensor may be directed to the tunnel. In some embodiments, sensors may direct sensing features, such as lenses for light sensors, to the housing channel 222.

In this embodiment, the IMD 200 has a series of lights, e.g. light emitting diodes (LEDs) 226. These may be individual LEDs or LED arrays. The LEDs 226 may each have a defined color or one or more LEDs 226 may be RGB (red, green, blue) LEDs to allow for each LED to show multiple color options. In addition, LEDs 226 may each be configured to provide alternative display options, such as fading in and out, blinking, etc. In conjunction, the LEDs 226 may provide a coordinated display. For example, all four may light up, then one by one each LED 226 may dim.

The LEDs 226 may be used to indicate a status of the IMD 200. For example, one LED 226 may indicate device operation status (e.g. active or inactive). Another LED 226 may show battery health (e.g., green for full, yellow for reduced and red as nearing empty). A third LED 226 may show data storage activity (e.g., the light may be on when logging data into onboard memory). Finally, the fourth LED 226 may indicate a communication status (e.g., a blue light may indicate that communication with a networked system is in process).

The IMD 200 also includes buttons 230 and 232. These may be used for user controls or information gathering. For example, the user may press button 230 to indicate they are in a happy or positive mood or button 232 to indicate they are in a sad or negative mood. In some embodiments, the number of presses of buttons 230 and 232 may indicate the level of happiness or sadness a user currently feels. For example, the user may press button 230 three times to indicate they are very happy. Alternatively, they may press the button 232 once to indicate that they are mildly depressed. The IMD 200 may prompt a user to select options at different times during treatment. For example, buttons 230 and 232 may flash when the IMD 200 is attached to a tube, when the user begins treatment and when the user completes treatment.

Figure 3:
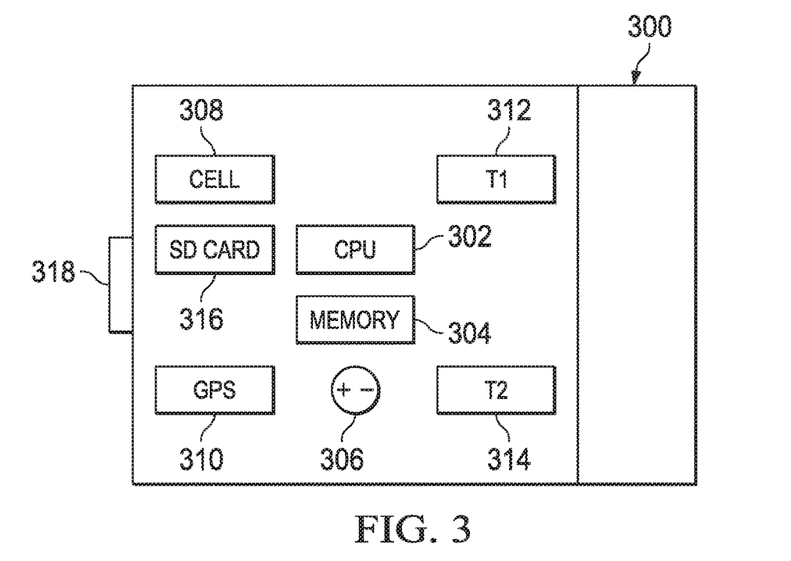
FIG. 3 is a block diagram of an embodiment of the infusion monitoring device.

FIG. 3 provides a block diagram of an infusion monitoring device 300. In this embodiment, the IMD 300 includes a central processing unit (CPU) 302, memory 304, power source 306, communication circuit 308, global positioning satellite system (GPS) receiver 310, temperature sensor 312, temperature sensor 314, removable memory 316 and a user interface 318.

Embodiments may also include alternative or additional components. For example, the IMD 300 may include a pressure sensor to confirm if the IMD 300 is connected to a tube. A pressure sensor may also be included to determine if pressure in the tube changes. In addition, the tube sensor could include a bubble sensor to determine if a bubble passes through the tube. A flow sensor may be used to determine if the fluid is flowing through the tube.

The control circuit 302 is shown as a CPU and may be a microprocessor, a microcontroller, programmable integrated circuit or other computer chip. The control circuit 302 is programmed or configured to access a program with operational instructions. In some embodiments, the control circuit 302 may include an integrated memory component with operational programs. The control circuit 302 is connected to a memory 304, which may store data logging instructions, analysis instructions, compliance standards and data obtained by sensors in the IMD 300. The control circuit 302 circuit may be directly wired to the memory 304 or indirectly connected through a bus or another component. The control circuit 302 circuit is also connected directly or indirectly with the communication circuit 308, the GPS receiver 310, temperature sensors 312 and 314, and user interface 318.

In some embodiments, the IMD 300 also includes a removable memory 316, such as an SD card, in addition to the memory 304. In some embodiments, the memory 304 may be an onboard memory for operational instructions and the removable memory 316 may receive and store data obtained during operation, such as sensor information, user interface information and any additional device logging data. In such embodiments, the IMD 300 may be returned to a facility, the removable memory 316 taken out and replaced with a new removable memory 316. The IMD 300 with the new removable memory 316 may be sent to another user without any risk of user data being transferred. In some embodiments, the IMD 300 may only include one form of memory 304 or removable memory 316. In other embodiments, the IMD 300 may include a plurality of memory components. Memory 304 and removable memory 316 may be random access memory, read only memory, programmable read only memory, programmable read-write memory, solid state memory or any other type of memory.

Power source 306 is also included to provide power to each component in the IMD. The power source 306 may be a battery, such as a lithium-ion button cell, or another power storage component.

The communication circuit 308 refers collectively to communication structures, including the communication chip and antenna. In this embodiment, communication circuit 308 is depicted as a cellular communication chip. Examples of communication modules 308 include BLUETOOTH communication modules, Wi-Fi communication modules, cellular communication modules and other communication network modules. In this embodiment, the communication circuit 308 may be a cellular network card that provides communication on the cellular network.

In this embodiment, the IMD 300 includes a GPS receiver 310, which determines the location of the IMD 300. Other embodiments may use alternative location determination circuits or systems. For example, communication systems may be used to identify a position of IMD 300 through a number of known techniques, such as triangulation to from known locations. The local receiver or structural component for the location determination systems within the device may be referred to as a position determining receiver.

This IMD 300 includes two temperature sensors 312 and 314, which are spaced apart along a channel or tunnel of the IMD 300. Temperature sensors 312 and 314 may be any type of contact or non-contact temperature gauge operable to measure temperature, such as a thermometer, thermistor, thermocouple, resistance temperature detector and semiconductor-based temperature sensor. In some embodiments, the temperature sensors 312 and 314 are the same type of sensor. In other embodiments, the temperature sensors 312 and 314 are different sensor types.

When the IMD 300 is attached to a tube, the temperature sensors 312 and 314 take the temperature periodically and the sensor data is recorded in the memory 304. In some embodiments, the temperature sensors 312 and 314 incorporate hardware, firmware or software to convert the sensed information into a temperature output before the sensor data is stored in memory 304. In other embodiments, the temperature conversion may occur within the control circuit 302. In yet other embodiments, the recorded data (such as current or voltage) may be maintained and the temperature gradient analysis would use the recorded data without converting it to a temperature output.

The user interface 318 on the IMD 300 may be any type of user interface, such as one or more buttons, switches, touch screen controls, knobs, voice-activated controls. The user interface 318 may include input and output components. Output components may include visual outputs, such as lights and displays, audio outputs, tactile outputs, vibratory outputs or other outputs to communicate information to a user. In some embodiments, the user interface 318 may be facilitated through the communication circuit 308. For example, a user may provide inputs through a phone application. Those inputs may be sent from the phone to the communication circuit 308 of the IMD 300. In addition, the communication circuit 308 may send outputs to the user's phone. For instance, the communication circuit 308 may send an alert that the IMD 300 has been attached to a tube. The IMD 300 may subsequently send a notice to the user's phone when the temperature sensors 312 and 314 indicate the medicine is ready for administration.

The user interface 318 may be used for operational controls or user inputs for information gathering. Examples of operation controls include an on/off control, start/stop control, communication control, timer control or any other control for the operation of the IMD 300. Information gathering options may include input controls to allow a user to provide identification data, social information (such as mood information) or other data separate from the operation of the IMD 300.

Figure 4:
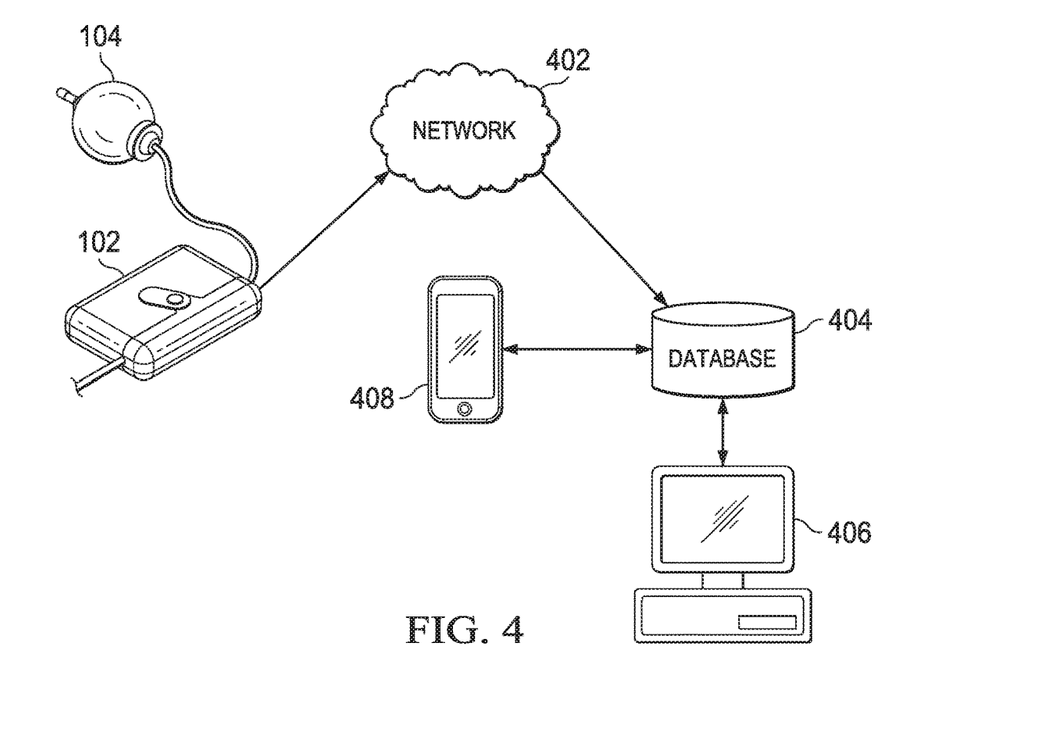
FIG. 4 is an embodiment of a compliance system with the infusion monitoring device.

FIG. 4 illustrates a networked system for the IMD 102 attached to the infusion pump 104. In addition to the IMD 102, the system shown includes network 402, database 404, a compliance computer 406 and mobile device 408. The IMD 102 includes a communication component to communicate with a network 402. This communication may be a direct connection, such as a cellular connection to the Internet, or an indirect connection, such as a WIFI connection to a networked router, which provides access to the Internet.

The network 402 may be any type of network that facilitates remote communication. For example, the network 402 may be the Internet. In some embodiments, the network 402 is integrated with the database 404 as part of a larger cloud-based network housing and aggregating data. In some embodiments, the database 404 may be independent from the larger network 402 or the database 404 may comprise a portion within network 402 and a portion at a standalone server or computer location.

The compliance computer 406 may be a smart-phone, laptop, desktop, tablet or other computer. The compliance computer 406 evaluates data from the database 404 to determine if the user properly administered their medication. In addition to compliance evaluations, the compliance computer 406 may also evaluate data for other information. For example, the compliance computer may evaluate social indications received from the user of IMD 102 to determine whether a person's indicated mood correlates to compliance with a treatment plan. These social indications may also influence whether a personal visit, call or communication may be scheduled to address matters unrelated to compliance.

The mobile device 408 may be any type of mobile device, such as a smart-phone, tablet, laptop computer, etc. The mobile device 408 may be any device used in connection with the administration of a patient's medication, such as a patient or the patient's clinician, representative or agent. The user's mobile device 408 may receive notices from the database reflecting their compliance, reminders and other information. For example, once the compliance computer 406 transmits a confirmation to database 404 that the user has administered treatment properly, the database 404 may send a positive feedback response to the mobile device 408, reinforcing the successful treatment. In some embodiments, the database 404 may have a trigger for sending reminders at a specified time after a first treatment. For example, eight hours after a morning treatment, the database 404 may send a reminder to the mobile device 408 to pull out the next infusion pump 104 and attach the IMD 102.

Those skilled in the art will recognize that this is an example of a networked system. The system may be implemented with other networks, connection points, components and organization. For example, the system may be built in a cloud environment with the network 402, database 404 and compliance computer 406 as integrated components. The system may automatically aggregate data received from the IMD 102 into the cloud database 404 and run a compliance check through a cloud-based compliance computer 406. Following the compliance check, the system may send the notice or other output to the mobile device 408.

When a patient is released from a medical facility for remote administration of medication, the patient may be referred for home infusion. The home infusion vendor will seek authorization from the payor and submit necessary data for the compliance system database 404.

The data will contain the medical treatment plan for the patient, such as the type and amount of medicine, treatment period and schedule, and contact information for the user, clinician, home infusion vendor agent for house calls or other authorized person. Those skilled in the art will recognize that other information may be needed for certain circumstances, such as separate medical dosage guidelines, medicine overviews, customized adjustments to the treatment plans, social analysis baseline information and other information. The data may be stored and organized within the database 404.

In some embodiments, this data may be encrypted and de-identified to the extent possible to protect patient data. In some embodiments, the patient identification information may remain in the home infusion vendor's database and only be made available when a notice is being sent. In such a case, the assigned IMD 102, treatment plan and necessary data in the compliance system may be associated with a secure identifier that is independent from personal information.

Upon receiving the IMD 102 request and relevant data, the compliance service assigns a unique identifier to the IMD 102 for all compliance checks and sends the IMD 102 along with instructional information for using the IMD 102. In some embodiments, the compliance service may have the number for the user's mobile device 408 and may send instructional information to the user via the mobile device 408. This process may include requesting any additional information to set-up the account. In some circumstances, the home infusion vendor or compliance service may deliver the IMD 102 with a first application to teach or demonstrate how to use the IMD 102 and the infusion pump 104.

To use the IMD 102, the patient may remove an infusion pump 104 from a freezer or refrigerator and attach the IMD 102 to a tube 106, which extends from the infusion pump 104. For example, cap 112 is opened, the tube 106 is aligned in the channels which form the tunnel 116 and then the cap 112 is closed. In some embodiments, the IMD 102 may include a verification component, such as a camera, a radio tag reader, optical reader, or other verification feature. For example, a camera may be used to verify that the patient has selected the correct medication, such as by taking a picture of the infusion pump 104. As another example, the camera may be used to read a medication code on the infusion pump 104 and provide an output to indicate that the medication corresponds to the patient's treatment plan. The verification component may be built anywhere into the housing of IMD 102 and facing outward. In some embodiments, the verification component may be on the top of the IMD 102 and a patient code may be attached to the bottom of the infusion pump 104. When the IMD 102 is properly attached to the tube, the verification component may be able read the patient code to confirm proper medication for the treatment. The verification information may be sent to the network 402 and stored in database 404.

Once the IMD 102 is attached to the tube 106, it may begin measuring the temperature of the tube 106. The IMD 102 may also store a beginning time for when the IMD 102 is attached to a tube. In other embodiments, the IMD 102 may begin measuring temperature when the cap 112 opens in order to first determine an ambient room temperature.

The IMD 102 will continue to measure the tube temperature at a given test rate, such as every 3 milliseconds, every second, three times per minute or any other rate. The default rate may be based upon expected rate of temperature changes, the power usage, the medication, treatment timeline and other factors. For example, if the medication is known to change only one degree per second at an average room temperature, then the default rate may be every 10 milliseconds so that the IMD 102 will capture enough readings to track the change in temperature without taking numerous readings at the same temperature. The default rate may be reduced to every 25 milliseconds if the IMD 102 will be deployed for an extended treatment plan in order to reduce power usage and extend the battery life for the IMD 102. The rate may also vary during operation based on current battery charge, current temperature, expected treatment timeline and other factors. For example, the rate of temperature readings may begin slowly because it will take time to increase the temperature in a proper manner and speed up as the temperature approaches the administration temperature for that medicine.

During operation, the IMD 102 may send data to the network 402. In some embodiments, the data may include notices for when the IMD 102 was connected to the tube 106, if a temperature spike occurred, when the medication began to flow, when the IMD 102 was removed and other notices. The data may also include the social button indications for mood or other personal indications from the user. The complete log of temperature readings stored on the removable memory may be sent at the end of the treatment. In some embodiments, the temperature readings may be periodically sent in small packets, such as a packet of temperature readings every two minutes.

The IMD 102 may collect specific times associated with the beginning (i.e., attachment to the tube), start of treatment and end of treatment. These times may be determined by the opening and closing of the clip, starting flow of the medication and ending flow of the medication. The IMD 102 may include bubble sensors, flow rate monitors and other features to monitor the operation of the infusion pump 104.

In other embodiments, the IMD 102 may only send notices when the compliance computer 406 sends a request for a detailed data log. For example, the IMD 102 may send discrete temperature measurements and timing information that correlates to the removal of the infusion pump 104 from storage and the beginning of a user's treatment. The compliance computer 406 may confirm if the timing and temperature information is consistent with treatment compliance. If it is inconsistent or the compliance computer 406 includes a flag to audit treatments, the compliance computer 406 may send a request to the IMD 102 for a specified data set.

If the data is in storage associated with the network 402 apart from the database 404, the data may also be sent to database 404 for further processing and analysis by the compliance computer 406. The compliance computer 406 may be associated with a compliance monitoring company, which may be independent or part of an infusion system provider, an insurance company or a medical facility.

In some embodiments, the database 404 receives notices and temperature data in near real time to the treatment and the compliance computer 406 conducts compliance checks for that user's treatment plan. A compliance check may include confirming that medication was removed from storage in the appropriate timeframe to allow the medication to warm up by the treatment window. It may also confirm that the treatment began within a given treatment window. For example, for a patient treatment plan that has a morning treatment at 8 a.m., the compliance check may confirm that the IMD 102 was attached to the infusion pump between 6:45 and 7:15 and the treatment began between 30 and 45 minutes after the IMD was attached. If the treatment plan calls for treatments every 12 hours, the window may adjust following the prior treatment. For example, if the first treatment is scheduled for 8 a.m. and the user administers the treatment late at 9 a.m., the next treatment will be scheduled by the compliance computer 406 for 9 p.m. The database 404 may store the updated schedule information set by the compliance computer 406.

The compliance check will also track the temperature gradient change logged by the IMD 102 and compare the gradient change pattern with gradient change patterns stored in database 404 to ensure that the temperature change was consistent with expected changes in temperature for the specified medication. Each medication may have an anticipated temperature gradient pattern when it is removed from cooled storage and placed into an ambient room temperature environment. The database 404 may contain a plurality of temperature gradient patterns for multiple medicines, starting temperatures, ambient temperatures and treatment temperatures.

The compliance computer 406 may determine a baseline gradient pattern by selecting a set of baseline gradient patterns having starting tube temperatures and ambient room temperatures close to the corresponding data points from the IMD 102 and averaging the gradient patterns. The compliance computer 406 may then compare the baseline gradient pattern to the current gradient pattern from IMD 102. If the current gradient pattern is the same or within a set deviation of the base gradient pattern, the compliance computer 406 will determine the treatment process for pulling the infusion pump 104 from storage and allowing the medication to reach the treatment temperature. The allowable deviation may be based upon a deviation analysis of multiple similarly situated gradient patterns. Upon this determination, the compliance computer 406 may update the database 404 to reflect the user followed the proper process. If the user followed the proper process and met other compliance requirements (e.g., time of treatment, duration of treatment, etc.), the system may send a positive message to the patient or care giver to encourage further compliance throughout the process. For example, the system may send text messages to the user's mobile device 408 and a care giver's phone indicating the successful treatment.

If the current gradient pattern is more than an allowable deviation from the anticipated gradient pattern, the compliance computer 406 will create an alert in the database, identifying the deviation. The compliance computer 406 may determine that the deviation indicates an error in handling, inadvertent noncompliance or intentional noncompliance and set the alert based on this determination. For example, if the infusion pump 104 was inadvertently placed on a warmer surface than the ambient temperature but not so hot as to damage the medication, the deviation in the gradient pattern may show a quick rise in temperature early in the process that settles back to the anticipated pattern such that the treatment administration appears consistent with an expected timeline and appropriate temperature change. The compliance computer 406 may determine that the skewed gradient pattern does not indicate interference with the overall compliance of the treatment. In such a case, the compliance computer 406 may update the database 404 with a flag to check for a reoccurring pattern showing this deviation. The first time the skewed pattern is determined, the system may provide the same positive compliance output. But if a pattern emerges, a compliance contact may receive a notice to look into the matter further to determine why this deviation is occurring.

For another example, the compliance computer 406 may determine that IMD 102 data shows that the user began treatment before the temperature rose sufficiently. The pattern of use may indicate that this error was not an intentional effort to be noncompliant. For example, if the database 404 shows a history of compliant and proper use of the IMD 102 and infusion pump 104, this single minor instance of noncompliance may be categorized as inadvertent. The compliance computer 406 may update the database 404 to show noncompliance and an inadvertent categorization. The system may then send to the patient's mobile device 408 a positive response with an added reminder to allow the infusion pump 104 to reach the proper temperature.

For another example, the compliance computer 406 may determine that a user was intentionally noncompliant. For example, the IMD 102 data may show that the medication flowed at a faster rate than expected and began to flow before the temperature approached the correct administration temperature. As another example, the data may indicate that the temperature increased at a high rate of speed, which indicates the medication may be harmed from high temperature exposure. If the compliance computer 406, determines these or other data indicates intentional noncompliance, it will update the database 404 with an alert to notify the home care vendor, medical facility or other parties to address the issue. In addition, the system may send a response to the user indicating that the last treatment did not follow the anticipated process. This may be presented as a motivational text to mobile phone 408 to encourage the user to follow the treatment plan properly.

The system may also send updates to the homecare provider, insurance company, medical facility or other group that is authorized to receive compliance updates. The system may also create reports for interested parties. The reports may be used for improved medical treatment and other purposes. For example, a positive compliance report in a medical file may allow the doctor to adjust and improve a treatment plan if the patient returns. In contrast, a negative compliance report may indicate that the medication plan may be appropriate, but a new administration method or additional oversight may be necessary for the medication plan to be successful.

The system may also use social responses from the user to help tailor the responses to best fit the patient's indicated outlook. In some applications, the patient will provide a psychosocial survey to establish a baseline from which additional indications throughout the treatment plan may be analyzed. The responses and visitation schedules may be established based on the psychosocial analysis and compliance patterns obtained through the IMD 102 for the purpose of increasing user compliance for the medical treatments.

The system may continue to evolve the comparison data within database 404 and increase accuracy of the anticipated temperature gradient by aggregating and analyzing the incoming temperature gradients over time. The database 404 may limit the aggregation of new gradient patterns to those that have been flagged as correlating to compliant treatments. The system may de-identify all temperature gradient information that is built into the aggregated system.

In addition, the system will continue to learn aggregated user patterns and user-specific patterns from the infusion monitoring devices. Based on these patterns, which may continue to evolve, the system will modify communication activity for the users. If the system detects a likelihood that a compliance issue may arise at a certain interval for a specific medication, the system may send a notification ahead of the interval to encourage a patient to continue complying with the treatment plan. For example, a ten-day treatment plan for an anti-biotic may often result in compliance issues on day seven when many patients are feeling better and feel compliance is no longer necessary. The system may send a reminder that proper completion of the ten-day plan is needed to help prevent a relapse. As another example, the system may recognize that a pattern of social indications often indicates probable compliance issues and increase communications to encourage compliance. Alternatively, certain results may indicate a pattern of successful compliance that does not benefit from additional communication and reminders.

Figure 5:
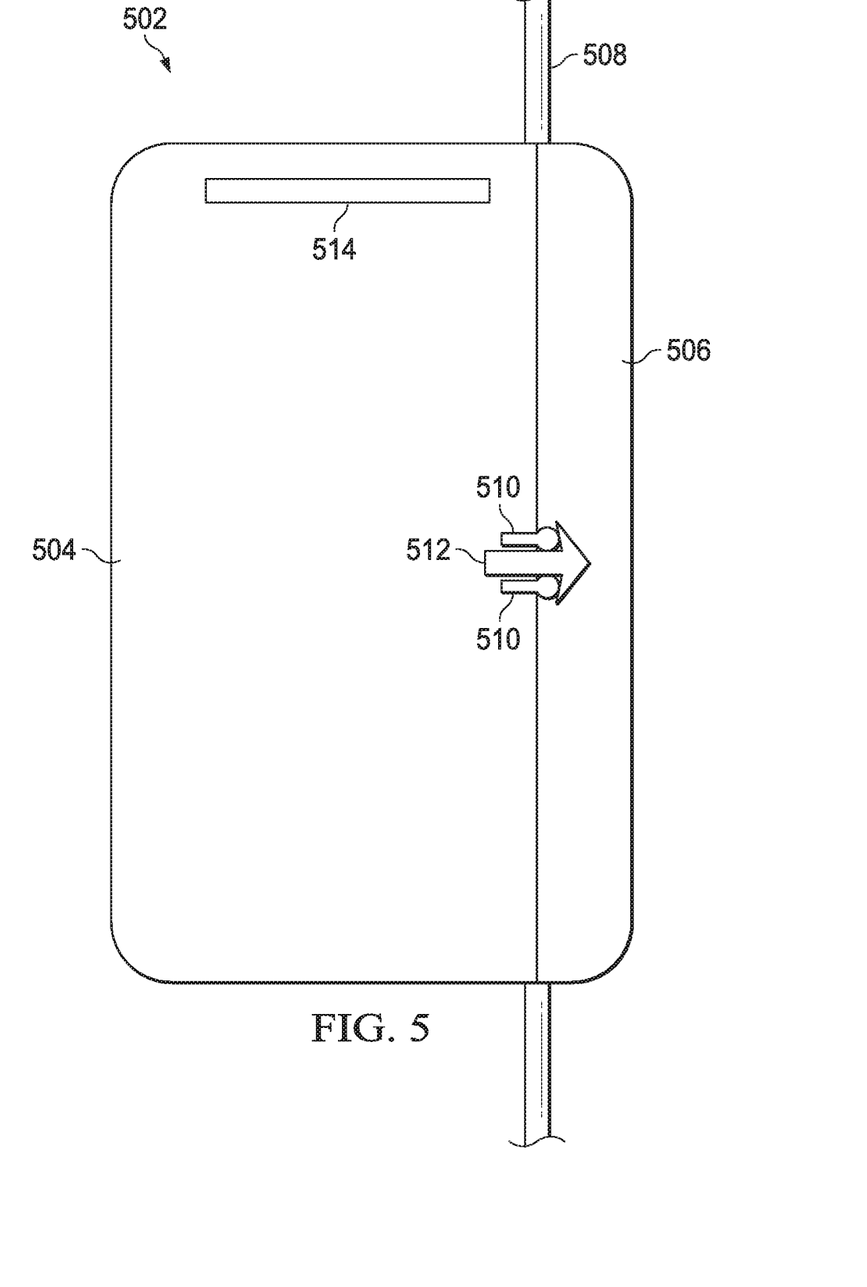
FIG. 5 is another embodiment of a infusion monitoring device.

FIG. 5 illustrates another embodiment of an infusion monitoring device 502. Similar to IMD 102, this embodiment includes a main body 504 and a cap 506. The IMD 502 is shown in a closed configuration with the cap 506 abutting the main body 504 around the tube 508. The cap 506 may be connected to the main body 504 with a slide connection, hinge connection, flexible connection or other connection. In some embodiments, the cap 506 may include a spring or other resilient component to bias the cap 506 to the closed position abutting the side of the main body 504. This embodiment of the IMD 502 includes a latch to hold the cap 506 in place once it is in a closed position. The latch comprises two protrusions 510 attached to the cap 506 and an arrow protrusion 512 extending from the main body 504. When the cap 506 is shut around a tube 508, the protrusions 510 pass by the sides of arrow protrusion 512, which flex inward to allow the protrusions to pass. The sides of the arrow protrusion 512 then flex back to an open position behind the protrusions 510 to prevent the cap 506 from opening. In some embodiments, the latch may be configured to hold the cap 506 in place during operation, but allows a user to reopen the cap 506 to remove the tube 508 and use the IMD 502 on another infusion pump.

In this embodiment, the IMD 502 has a visual output 514, which may be a light array, light bar or a display. The visual output 514 may be sectioned to allow different visual information to be presented along the bar in some embodiments. The visual output 514 may also provide feedback information as a display with an alphanumeric output. As discussed with FIG. 2, visual output 514 may provide different lighting characteristics to indicate various status information.

The invention being thus described and further described in the claims, it will be obvious that the same may be varied in many ways. Such variations are not to be regarded as a departure from the spirit and scope of the invention, and all such modifications as would be obvious to one skilled in the art are intended to be included within the scope of the apparatus and method described.

The invention claimed is:

1. An infusion pump compliance system, comprising:
an infusion monitoring device comprising:
a housing having a main body and a cap attached thereto, wherein the cap is movable between a closed position and an open position and the cap includes a cap channel in a surface facing the main body and the main body includes a housing channel corresponding to the cap channel,
wherein the cap channel and housing channel form a tunnel when the cap is in the closed position,
a control circuit within the housing,
a memory within the housing that is connected to the control circuit,
a user interface on the housing that is connected to the control circuit,
a communication circuit within the housing that is connected to the control circuit, wherein the communication circuit facilitates wireless communication with a network, and
a temperature sensor connected to the control circuit, wherein the temperature sensor is positioned within the housing adjacent to the tunnel and configured to measure temperature in the tunnel; and a compliance system network, comprising:
a database in communication with the network, wherein the database stores a patient treatment plan and a baseline temperature gradient pattern for a medication identified in the patient treatment plan; and
a compliance computer having a network communication circuit and an analysis circuit;
wherein during operation of the infusion pump medical treatment compliance system, the infusion monitoring device is attached to a tube extending from an infusion pump, whereby the housing grips the tube in the tunnel and the temperature sensor measures temperature of the tube;
wherein the control circuit receives temperature measurements from the temperature sensor on a periodic basis and stores the temperature measurements in the memory, wherein the control circuit sends the temperature measurements to the network using the communication circuit, wherein the temperature measurements taken from a starting time to an end time of a medication treatment and collectively form an infusion monitoring device temperature gradient pattern;
wherein the compliance computer determines a compliance status based on whether the infusion monitoring device indicates treatment compliance, wherein the treatment compliance is determined by comparing the infusion monitoring device temperature gradient pattern with the baseline temperature gradient pattern, wherein gradient pattern consistency indicates compliance and gradient pattern inconsistency indicates non-compliance; and
wherein the compliance computer generates a compliance notification providing feedback based on the compliance status.

2. The infusion pump medical treatment compliance system of claim 1, wherein the infusion monitoring device further comprises a location determination circuit, which identifies a location of the infusion monitoring device at the starting time of the medication treatment.

3. The infusion pump medical treatment compliance system of claim 1, wherein the control circuit of the infusion monitoring device sends the starting time of the medication treatment to the network, and the compliance computer compares the starting time to a scheduled starting time within the patient treatment plan to determine if the medication treatment complied with the patient treatment plan.

4. The infusion pump medical treatment compliance system of claim 1, wherein the network communication circuit of the compliance computer sends the compliance notification to the infusion monitoring device for output to a user of the infusion monitoring device via the user interface.

5. The infusion pump medical treatment compliance system of claim 1, wherein the network communication circuit of the compliance system computer sends the compliance notification to a mobile device associated with a user of the infusion monitoring device via the user interface.

6. The infusion pump medical treatment compliance system of claim 1, wherein the user interface collects social feedback from a user of the infusion monitoring device, and wherein the compliance notification is also based on the social feedback.

7. An infusion monitoring device, comprising:
a housing having a main body and a cap attached thereto, wherein the cap is movable between a closed position and an open position and the cap includes a cap channel in a surface facing the main body and the main body includes a housing channel corresponding to the cap channel, wherein the cap channel and the housing channel form a tunnel when the cap is in the closed position;

a control circuit within the housing;

a memory within the housing that is connected to the control circuit, wherein the memory is removable;

a user interface on the housing that is connected to the control circuit;

a communication circuit within the housing that is connected to the control circuit, wherein the communication circuit facilitates wireless communication with a network; and a temperature sensor connected to the control circuit, wherein the temperature sensor is positioned within the housing adjacent to the tunnel and configured to measure temperature in the tunnel;

wherein during operation of the infusion monitoring device, the housing is attached to a tube extending from an infusion pump, whereby the housing grips the tube in the tunnel between the cap and the main body and the temperature sensor measures temperature of the tube;

wherein the control circuit receives temperature measurements from the temperature sensor on a periodic basis and stores the temperature measurements in the memory, wherein the temperature measurements form an infusion monitoring device temperature gradient pattern; and wherein the control circuit sends the temperature measurements to the network using the communication circuit.

8. The infusion monitoring device of claim 7, comprising a location determination circuit, wherein the control circuit receives a location of the infusion monitoring device from the location determination circuit when the infusion monitoring device is attached to the tube.

9. The infusion monitoring device of claim 7, wherein the memory stores patient treatment plan information and a baseline temperature gradient pattern, wherein the control circuit compares the baseline temperature gradient pattern with the infusion monitoring device temperature gradient pattern to determine if a user complied with medical treatment, and the control circuit outputs a compliance indication on the user interface.

10. The infusion monitoring device of claim 9, wherein the control circuit compares the patient treatment plan information with operation data of the infusion monitoring device to determine if a user complied with the patient treatment plan information, and the compliance indication is further based on compliance with the parameters.

11. A method for remotely monitoring patient compliance with infusion pump medical treatments, comprising:

receiving a patient treatment plan for a patient in a compliance system network, wherein the patient treatment plan provides a medication and a treatment, and wherein the compliance system network includes a database and a compliance computer having a network communication circuit and an analysis circuit, and the database stores a plurality of baseline temperature gradient patterns, wherein each of the plurality of baseline temperature gradient patterns is for the medication;

associating an infusion monitoring device with the patient using an IMD code, wherein the infusion monitoring device comprises:
a housing that includes a tunnel configured to fit around a tube that extends from an infusion pump, a control circuit within the housing, a memory within the housing that is connected to the control circuit, a communication circuit within the housing that is connected to the control circuit, wherein the communication circuit facilitates wireless communication with a network, and a temperature sensor that is connected to the control circuit, wherein the temperature sensor is positioned within the housing adjacent to the tunnel and configured to measure temperature in the tunnel;

wherein during operation of the infusion monitoring device, the control circuit receives temperature measurements from the temperature sensor on a periodic basis from a starting time to an end time of an infusion pump treatment, and the temperature measurements collectively form an infusion monitoring device temperature gradient pattern;

receiving the IMD code and the infusion monitoring device temperature gradient pattern from the infusion monitoring device in the compliance computer;

identifying the patient treatment plan within the database that corresponds to the infusion monitoring device by the IMD code;

comparing the infusion monitoring device temperature gradient pattern with the baseline temperature gradient pattern for the medication identified in the patient treatment plan to identify gradient pattern deviations;

determining a compliance status based on whether the gradient pattern deviations indicates the patient complied with the treatment provided in the patient treatment plan, wherein the gradient pattern deviations within a threshold indicate compliance and the gradient pattern deviations outside a threshold indicate noncompliance; and generating, by the compliance computer, a compliance notification based on the compliance status.

12. The method for remotely monitoring patient compliance with infusion pump medical treatments of claim 11, wherein the infusion monitoring device further comprises a location determination circuit, which identifies a location of the infusion monitoring device at the starting time of the infusion pump treatment.

13. The method for remotely monitoring patient compliance with infusion pump medical treatments of claim 11, further comprising:

receiving the starting time of the infusion pump treatment through the network; and comparing the starting time to a scheduled starting time within the patient treatment plan to determine if the patient treatment complied with the patient treatment plan.

14. The method for remotely monitoring patient compliance with infusion pump medical treatments of claim 13, further comprising:

updating a schedule for a following infusion pump treatment within the patient treatment plan based on the starting time of the infusion pump treatment.

15. An infusion monitoring device, comprising:

a housing having a main body and a cap attached thereto, wherein the cap is movable between a closed position and an open position and the cap includes a cap channel in a surface facing the main body and the main body includes a housing channel corresponding to the cap channel, wherein the cap channel and the housing channel form a tunnel when the cap is in the closed position;

a control circuit within the housing;

a memory within the housing that is connected to the control circuit;

a user interface on the housing that is connected to the control circuit;

a communication circuit within the housing that is connected to the control circuit, wherein the communication circuit facilitates wireless communication with a network; and a temperature sensor connected to the control circuit, wherein the temperature sensor is positioned within the housing adjacent to the tunnel and configured to measure temperature in the tunnel;

wherein during operation of the infusion monitoring device, the housing is attached to a tube extending from an infusion pump, whereby the housing grips the tube in the tunnel between the cap and the main body and the temperature sensor measures temperature of the tube;

wherein the control circuit receives temperature measurements from the temperature sensor on a periodic basis and stores the temperature measurements in the memory, wherein the temperature measurements form an infusion monitoring device temperature gradient pattern;

wherein the control circuit sends the temperature measurements to the network using the communication circuit; and wherein the memory stores patient treatment plan information and a baseline temperature gradient pattern, wherein the control circuit compares the baseline temperature gradient pattern with the infusion monitoring device temperature gradient pattern to determine if a user complied with medical treatment, and the control circuit outputs a compliance indication on the user interface.

16. The infusion monitoring device of claim 15, comprising a location determination circuit, wherein the control circuit receives a location of the infusion monitoring device from the location determination circuit when the infusion monitoring device is attached to the tube.

17. The infusion monitoring device of claim 15, wherein the memory is removable.

18. The infusion monitoring device of claim 15, wherein the control circuit compares the patient treatment plan information with operation data of the infusion monitoring device to determine if a user complied with the patient treatment plan information, and the compliance indication is further based on compliance with the parameters.

* * * * *

UNITED STATES PATENT AND TRADEMARK OFFICE
CERTIFICATE OF CORRECTION

PATENT NO. : 10,825,560 B1  
APPLICATION NO. : 16/733492  
DATED : November 3, 2020  
INVENTOR(S) : Mitchell Thomas Berenson Page 1 of 2

It is certified that error appears in the above-identified patent and that said Letters Patent is hereby corrected as shown below:

In the Specification

Column 1, Line 13: insert --a-- between "such as" and "hospital"

Column 1, Lines 17-18: delete "proscribed" and insert --prescribed--

Column 3, Line 50: delete "proscribed" and insert --prescribed--

Column 4, Line 1: delete "a" and insert --an--

Column 4, Line 56: insert --an-- between "such" and "embodiment"

Column 4, Line 57: insert --to-- between "adjacent" and "the tunnel"

Column 4, Line 58: delete "It" and insert --If--

Column 6, Lines 28-29: delete "control circuit 302 circuit may" and insert --control circuit 302 may--

Column 6, Line 31: delete "control circuit 302 circuit is" and insert --control circuit 302 is--

Column 7, Line 35: insert --and-- between "knobs," and "voice-activated controls"

Column 8, Lines 30-31: insert --the mobile device 408 belonging to-- between "such as" and "a patient"

Column 8, Line 47: delete "organization" and insert --organizations--

Column 12, Line 11: delete "," between "computer 406" and "determines"

Column 12, Line 12: delete "indicates" and insert --indicate--

Signed and Sealed this  
Sixteenth Day of March, 2021

Drew Hirshfeld  
*Performing the Functions and Duties of the  
Under Secretary of Commerce for Intellectual Property and  
Director of the United States Patent and Trademark Office*

CERTIFICATE OF CORRECTION (continued)
U.S. Pat. No. 10,825,560 B1

In the Claims

Column 14, Lines 9-10, Claim 1: delete "medical treatment"

Column 14, Line 35, Claim 2: delete "medical treatment"

Column 14, Line 40, Claim 3: delete "medical treatment"

Column 14, Line 47, Claim 4: delete "medical treatment"

Column 14, Line 52, Claim 5: delete "medical treatment"

Column 14, Line 57, Claim 6: delete "medical treatment"

Column 15, Line 47, Claim 10: delete "a user" and insert --the user--

Column 15, Line 49, Claim 10: delete "parameters" and insert --patient treatment plan--

Column 16, Line 51, Claim 13: delete "treatment" between "patient" and "complied"

Column 18, Line 22, Claim 18: delete "a user" and insert --the user--

Column 18, Line 24, Claim 18: delete "parameters" and insert --patient treatment plan information--